(12) United States Patent
Figulla et al.

(10) Patent No.: US 8,062,355 B2
(45) Date of Patent: Nov. 22, 2011

(54) SELF-EXPANDABLE MEDICAL INSTRUMENT FOR TREATING DEFECTS IN A PATIENT'S HEART

(75) Inventors: Hans-Reiner Figulla, Jena (DE); Markus Ferrari, Jena (DE)

(73) Assignee: JenaValve Technology, Inc., Wilmington, DE (US)

( * ) Notice: Subject to any disclaimer, the term of this patent is extended or adjusted under 35 U.S.C. 154(b) by 467 days.

(21) Appl. No.: 11/592,369

(22) Filed: Nov. 3, 2006

(65) Prior Publication Data
US 2007/0142906 A1 Jun. 21, 2007

(30) Foreign Application Priority Data
Nov. 4, 2005 (DE) .................. 10 2005 052 628

(51) Int. Cl.
*A61F 2/06* (2006.01)
(52) U.S. Cl. ...... 623/2.1; 623/2.14; 623/2.17; 623/2.18; 623/1.24
(58) Field of Classification Search ............... 623/1.3, 623/1.31, 1.24, 1.26, 2.1–2.19; *A61F 2/06*
See application file for complete search history.

(56) References Cited

U.S. PATENT DOCUMENTS

| | | |
|---|---|---|
| 5,002,566 A | 3/1991 | Carpentier et al. |
| 5,035,706 A | 7/1991 | Giantureo et al. |
| 5,061,277 A | 10/1991 | Carpentier et al. |
| 5,094,661 A | 3/1992 | Levy et al. |
| 5,104,407 A | 4/1992 | Lam et al. |
| 5,197,979 A | 3/1993 | Quintero et al. |
| 5,279,612 A | 1/1994 | Eberhardt |
| 5,332,402 A | 7/1994 | Teitelbaum |
| 5,336,258 A | 8/1994 | Quintero et al. |
| 5,352,240 A | 10/1994 | Ross |

(Continued)

FOREIGN PATENT DOCUMENTS
AU 2006308187 A1 10/2006
(Continued)

OTHER PUBLICATIONS

File history for German Patent DE 195 46 692 filed Dec. 14, 1995 and patented Jul. 11, 2002.

(Continued)

*Primary Examiner* — Thomas J Sweet
*Assistant Examiner* — Jason-Dennis Stewart
(74) *Attorney, Agent, or Firm* — Finnegan, Henderson, Farabow, Garrett & Dunner, LLP (57) ABSTRACT

The invention relates to a self-expandable medical instrument (100) for treating defects in a patient's heart, in particular for the transvascular implantation of a prosthetic heart valve (30), wherein the medical instrument (100) is introducible into the body of a patient in a minimally-invasive procedure using a catheter system (40) and comprises a stent (1) made of a flexible mesh (2) of thin wires or filaments (2'). In order to realize a positioning of medical instrument (100) in the patient's heart which is as precise as possible and to securely anchor same there, it is provided for the stent (1) composed of the flexible mesh (2) to exhibit in the expanded state of the medical instrument (100) a distal retention area (10) with a laterally-inverted beaded portion (12) which is engageable in at least one pocket (51) of the patient's defective heart valve (50), a proximal retention area (20), and a center area (15) positioned between the distal and the proximal retention area (10, 20).

42 Claims, 7 Drawing Sheets

U.S. PATENT DOCUMENTS

| | | |
|---|---|---|
| 5,368,608 A | 11/1994 | Levy et al. |
| 5,411,552 A | 5/1995 | Andersen et al. |
| 5,456,713 A | 10/1995 | Chuter |
| 5,509,930 A | 4/1996 | Love |
| 5,549,666 A | 8/1996 | Hata et al. |
| 5,595,571 A | 1/1997 | Jaffe et al. |
| 5,613,982 A | 3/1997 | Goldstein |
| 5,632,778 A | 5/1997 | Goldstein |
| 5,674,298 A | 10/1997 | Levy et al. |
| 5,679,112 A | 10/1997 | Levy et al. |
| 5,683,451 A | 11/1997 | Lenker et al. |
| 5,697,972 A | 12/1997 | Kim et al. |
| 5,713,953 A | 2/1998 | Vallana et al. |
| 5,746,775 A | 5/1998 | Levy et al. |
| 5,755,777 A | 5/1998 | Chuter |
| 5,824,041 A | 10/1998 | Lenker et al. |
| 5,824,080 A | 10/1998 | Lamuraglia |
| 5,840,081 A | 11/1998 | Andersen et al. |
| 5,841,382 A | 11/1998 | Walden et al. |
| 5,843,181 A | 12/1998 | Jaffe et al. |
| 5,876,434 A | 3/1999 | Flomenblit et al. |
| 5,880,242 A | 3/1999 | Hu et al. |
| 5,899,936 A | 5/1999 | Goldstein |
| 5,928,281 A | 7/1999 | Huynh et al. |
| 5,935,163 A | 8/1999 | Gabbay |
| 5,104,407 A | 9/1999 | Lam et el. |
| 6,001,126 A | 12/1999 | Nguyen-Thien-Nhon |
| 5,061,277 A | 2/2000 | Carpentier et al. |
| 6,077,297 A | 6/2000 | Robinson et al. |
| 6,093,530 A | 7/2000 | McIlroy et al. |
| 6,102,944 A | 8/2000 | Huynh et al. |
| 6,117,169 A | 9/2000 | Moe |
| 6,120,534 A * | 9/2000 | Ruiz ............................ 623/1.19 |
| 6,126,685 A | 10/2000 | Lenker et al. |
| 6,168,614 B1 | 1/2001 | Andersen et al. |
| 6,177,514 B1 | 1/2001 | Pathak et al. |
| 6,183,481 B1 | 2/2001 | Lee et al. |
| 6,200,336 B1 | 3/2001 | Pavcnik et al. |
| 6,214,055 B1 | 4/2001 | Simionescu et al. |
| 6,231,602 B1 | 5/2001 | Carpentier et al. |
| 6,241,738 B1 | 6/2001 | Dereume |
| 6,254,564 B1 | 7/2001 | Wilk et al. |
| 6,254,636 B1 | 7/2001 | Peredo |
| 6,283,995 B1 | 9/2001 | Moe et al. |
| 6,287,338 B1 | 9/2001 | Sarnowski et al. |
| 6,338,740 B1 | 1/2002 | Carpentier |
| 6,342,070 B1 | 1/2002 | Nguyen-Thien-Nhon |
| 6,344,044 B1 | 2/2002 | Fulkerson et al. |
| 6,350,278 B1 | 2/2002 | Lenker et al. |
| 6,379,740 B1 | 4/2002 | Rinaldi et al. |
| 6,391,538 B1 | 5/2002 | Vyavahare et al. |
| 6,425,916 B1 | 7/2002 | Garrison et al. |
| 6,454,799 B1 | 9/2002 | Schreck et al. |
| 6,471,723 B1 | 10/2002 | Ashworth et al. |
| 6,478,819 B2 | 11/2002 | Moe |
| 6,508,833 B2 | 1/2003 | Pavcnik et al. |
| 6,509,145 B1 | 1/2003 | Torrianni |
| 6,521,179 B1 | 2/2003 | Girardot et al. |
| 6,540,782 B1 | 4/2003 | Snyders |
| 6,558,417 B2 | 5/2003 | Peredo |
| 6,558,418 B2 | 5/2003 | Carpentier et al. |
| 6,572,642 B2 | 6/2003 | Rinaldi et al. |
| 6,582,462 B1 | 6/2003 | Andersen et al. |
| 6,585,766 B1 | 7/2003 | Huynh et al. |
| 6,613,086 B1 | 9/2003 | Moe et al. |
| 6,682,559 B2 | 1/2004 | Myers et al. |
| 6,730,118 B2 | 5/2004 | Spenser et al. |
| 6,736,845 B2 | 5/2004 | Marquez et al. |
| 6,767,362 B2 | 7/2004 | Schreck |
| 6,790,230 B2 | 9/2004 | Beyersdorf et al. |
| 6,808,529 B2 | 10/2004 | Fulkerson |
| 6,821,211 B2 | 11/2004 | Otten et al. |
| 6,821,297 B2 | 11/2004 | Snyders |
| 6,824,970 B2 | 11/2004 | Vyavahare et al. |
| 6,830,584 B1 | 12/2004 | Seguin |
| 6,861,211 B2 | 3/2005 | Levy et al. |
| 6,872,226 B2 | 3/2005 | Cali et al. |
| 6,881,199 B2 | 4/2005 | Wilk et al. |
| 6,893,460 B2 | 5/2005 | Spenser et al. |
| 6,908,481 B2 | 6/2005 | Cribier |
| 6,911,043 B2 | 6/2005 | Myers et al. |
| 6,945,997 B2 | 9/2005 | Huynh et al. |
| 6,974,474 B2 | 12/2005 | Pavcnik et al. |
| 7,014,655 B2 | 3/2006 | Barbarash et al. |
| 7,018,406 B2 | 3/2006 | Seguin et al. |
| 7,037,333 B2 | 5/2006 | Myers et al. |
| 7,050,276 B2 | 5/2006 | Nishiyama |
| 7,078,163 B2 | 7/2006 | Torrianni |
| 7,081,132 B2 | 7/2006 | Cook et al. |
| 7,137,184 B2 | 11/2006 | Schreck |
| 7,141,064 B2 | 11/2006 | Scott et al. |
| 7,163,556 B2 | 1/2007 | Xie et al. |
| 7,189,259 B2 | 3/2007 | Simionescu et al. |
| 7,198,646 B2 | 4/2007 | Figulla et al. |
| 7,201,772 B2 | 4/2007 | Schwammenthal et al. |
| 7,238,200 B2 | 7/2007 | Lee et al. |
| 7,252,682 B2 | 8/2007 | Seguin |
| 7,318,278 B2 | 1/2008 | Zhang et al. |
| 7,318,998 B2 | 1/2008 | Goldstein et al. |
| 7,322,932 B2 | 1/2008 | Xie et al. |
| 7,329,278 B2 | 2/2008 | Seguin et al. |
| 7,381,218 B2 | 6/2008 | Schreck |
| 7,393,360 B2 | 7/2008 | Spenser et al. |
| 7,399,315 B2 | 7/2008 | Iobbi |
| 7,452,371 B2 | 11/2008 | Pavcnik et al. |
| 7,473,275 B2 | 1/2009 | Marquez |
| 2001/0011187 A1 | 8/2001 | Pavcnik et al. |
| 2001/0039450 A1 | 11/2001 | Pavcnik et al. |
| 2002/0032481 A1 | 3/2002 | Gabbay |
| 2002/0055775 A1 | 5/2002 | Carpentier et al. |
| 2002/0123790 A1 | 9/2002 | White et al. |
| 2002/0133226 A1 | 9/2002 | Marquez et al. |
| 2002/0143387 A1 | 10/2002 | Soetikno et al. |
| 2002/0198594 A1 | 12/2002 | Schreck |
| 2003/0027332 A1 | 2/2003 | Lafrance et al. |
| 2003/0036791 A1 | 2/2003 | Philipp et al. |
| 2003/0036795 A1 | 2/2003 | Andersen et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0114913 A1 | 6/2003 | Spenser et al. |
| 2003/0125795 A1 | 7/2003 | Pavcnik et al. |
| 2003/0139796 A1 | 7/2003 | Sequin et al. |
| 2003/0139803 A1 | 7/2003 | Sequin et al. |
| 2003/0149476 A1 | 8/2003 | Damm et al. |
| 2003/0153974 A1 | 8/2003 | Spenser et al. |
| 2003/0195620 A1 | 10/2003 | Huynh et al. |
| 2003/0236570 A1 | 12/2003 | Cook et al. |
| 2004/0006380 A1 | 1/2004 | Buck et al. |
| 2004/0039436 A1 | 2/2004 | Spenser et al. |
| 2004/0049262 A1 | 3/2004 | Obermiller et al. |
| 2004/0073289 A1 | 4/2004 | Hartley |
| 2004/0078950 A1 | 4/2004 | Schreck |
| 2004/0117004 A1 | 6/2004 | Osborne et al. |
| 2004/0117009 A1 | 6/2004 | Cali et al. |
| 2004/0148018 A1 | 7/2004 | Carpentier et al. |
| 2004/0153145 A1 | 8/2004 | Simionescu et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0193244 A1 | 9/2004 | Hartley et al. |
| 2004/0210301 A1 | 10/2004 | Obermiller et al. |
| 2004/0210304 A1 | 10/2004 | Seguin et al. |
| 2004/0260389 A1 | 12/2004 | Case et al. |
| 2005/0009000 A1 | 1/2005 | Wilhelm et al. |
| 2005/0033220 A1 | 2/2005 | Wilk et al. |
| 2005/0033398 A1 | 2/2005 | Seguin |
| 2005/0043790 A1 | 2/2005 | Seguin |
| 2005/0049692 A1 | 3/2005 | Numamoto et al. |
| 2005/0075725 A1* | 4/2005 | Rowe ............................ 623/2.14 |
| 2005/0075776 A1 | 4/2005 | Cho |
| 2005/0096726 A1 | 5/2005 | Sequin et al. |
| 2005/0096736 A1 | 5/2005 | Osse et al. |
| 2005/0098547 A1 | 5/2005 | Cali et al. |
| 2005/0113910 A1 | 5/2005 | Paniagua et al. |
| 2005/0119728 A1 | 6/2005 | Sarac |

| | | |
|---|---|---|
| 2005/0119736 A1 | 6/2005 | Zilla et al. |
| 2005/0125075 A1 | 6/2005 | Meade |
| 2005/0137687 A1 | 6/2005 | Salahieh et al. |
| 2005/0137688 A1* | 6/2005 | Salahieh et al. ............. 623/2.11 |
| 2005/0137690 A1 | 6/2005 | Salahieh et al. |
| 2005/0137697 A1 | 6/2005 | Salahieh et al. |
| 2005/0137698 A1 | 6/2005 | Salahieh et al. |
| 2005/0137702 A1 | 6/2005 | Haug et al. |
| 2005/0143804 A1 | 6/2005 | Haverkost |
| 2005/0143807 A1 | 6/2005 | Pavcnik et al. |
| 2005/0149166 A1 | 7/2005 | Schaeffer et al. |
| 2005/0150775 A1 | 7/2005 | Zhang et al. |
| 2005/0171597 A1 | 8/2005 | Boatman et al. |
| 2005/0171598 A1 | 8/2005 | Schaeffer |
| 2005/0192665 A1 | 9/2005 | Spenser et al. |
| 2005/0197695 A1 | 9/2005 | Stacchino et al. |
| 2005/0222668 A1 | 10/2005 | Schaeffer et al. |
| 2005/0234546 A1 | 10/2005 | Nugent et al. |
| 2005/0267560 A1 | 12/2005 | Bates |
| 2006/0009842 A1 | 1/2006 | Huynh et al. |
| 2006/0025857 A1 | 2/2006 | Bergheim et al. |
| 2006/0047343 A1 | 3/2006 | Oviatt et al. |
| 2006/0058864 A1 | 3/2006 | Schaeffer et al. |
| 2006/0064151 A1* | 3/2006 | Guterman et al. ............. 623/1.3 |
| 2006/0111770 A1 | 5/2006 | Pavcnik et al. |
| 2006/0142846 A1 | 6/2006 | Pavcnik et al. |
| 2006/0149360 A1 | 7/2006 | Schwammenthal et al. |
| 2006/0167543 A1 | 7/2006 | Bailey et al. |
| 2006/0193885 A1 | 8/2006 | Neethling et al. |
| 2006/0210597 A1 | 9/2006 | Hiles |
| 2006/0224183 A1 | 10/2006 | Freudenthal |
| 2006/0229718 A1 | 10/2006 | Marquez |
| 2006/0229719 A1 | 10/2006 | Marquez et al. |
| 2006/0246584 A1 | 11/2006 | Covelli |
| 2006/0259134 A1 | 11/2006 | Schwammenthal et al. |
| 2006/0259136 A1 | 11/2006 | Nguyen et al. |
| 2006/0265056 A1 | 11/2006 | Nguyen et al. |
| 2006/0287717 A1 | 12/2006 | Rowe et al. |
| 2006/0287719 A1 | 12/2006 | Rowe et al. |
| 2006/0290027 A1 | 12/2006 | O'Connor et al. |
| 2006/0293745 A1 | 12/2006 | Carpentier et al. |
| 2007/0005129 A1 | 1/2007 | Damm et al. |
| 2007/0005131 A1 | 1/2007 | Taylor |
| 2007/0005132 A1 | 1/2007 | Simionescu et al. |
| 2007/0020248 A1 | 1/2007 | Everaerts et al. |
| 2007/0021826 A1 | 1/2007 | Case et al. |
| 2007/0027535 A1 | 2/2007 | Purdy, Jr. et al. |
| 2007/0038291 A1 | 2/2007 | Case et al. |
| 2007/0038295 A1 | 2/2007 | Case et al. |
| 2007/0043435 A1 | 2/2007 | Seguin et al. |
| 2007/0050014 A1 | 3/2007 | Johnson |
| 2007/0088431 A1 | 4/2007 | Bourang et al. |
| 2007/0093887 A1 | 4/2007 | Case et al. |
| 2007/0100435 A1 | 5/2007 | Case et al. |
| 2007/0100440 A1 | 5/2007 | Figulla et al. |
| 2007/0112422 A1 | 5/2007 | Dehdashtian |
| 2007/0123700 A1 | 5/2007 | Ueda et al. |
| 2007/0123979 A1 | 5/2007 | Perier et al. |
| 2007/0142906 A1 | 6/2007 | Figulla et al. |
| 2007/0162103 A1 | 7/2007 | Case et al. |
| 2007/0173932 A1 | 7/2007 | Cali et al. |
| 2007/0179592 A1 | 8/2007 | Schaeffer |
| 2007/0185565 A1 | 8/2007 | Schwammenthal et al. |
| 2007/0203576 A1 | 8/2007 | Lee et al. |
| 2007/0213813 A1 | 9/2007 | Von Segesser et al. |
| 2007/0239271 A1 | 10/2007 | Nguyen |
| 2007/0244551 A1 | 10/2007 | Stobie |
| 2007/0260327 A1 | 11/2007 | Case et al. |
| 2007/0288087 A1 | 12/2007 | Fearnot et al. |
| 2008/0004688 A1 | 1/2008 | Spenser et al. |
| 2008/0021546 A1 | 1/2008 | Patz et al. |
| 2008/0033534 A1 | 2/2008 | Cook et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077236 A1 | 3/2008 | Letac et al. |
| 2008/0086205 A1 | 4/2008 | Gordy et al. |
| 2008/0097586 A1 | 4/2008 | Pavcnik et al. |
| 2008/0102439 A1 | 5/2008 | Tian et al. |
| 2008/0133003 A1 | 6/2008 | Seguin et al. |
| 2008/0140189 A1 | 6/2008 | Nguyen et al. |
| 2008/0154355 A1 | 6/2008 | Benichou et al. |
| 2008/0200977 A1 | 8/2008 | Paul et al. |
| 2008/0215143 A1 | 9/2008 | Seguin |
| 2008/0262602 A1 | 10/2008 | Wilk et al. |
| 2008/0269878 A1 | 10/2008 | Iobbi |
| 2008/0275549 A1 | 11/2008 | Rowe |

FOREIGN PATENT DOCUMENTS

| | | |
|---|---|---|
| CA | 2436258 A1 | 1/2005 |
| CA | 2595233 | 7/2006 |
| CA | 2627409 A1 | 5/2007 |
| DE | 195 46 692 A1 | 6/1997 |
| DE | 19546692 A1 | 6/1997 |
| DE | 20003874 U1 | 6/2000 |
| DE | 19857887 A1 | 7/2000 |
| DE | 10010073 A1 | 9/2001 |
| DE | 10010074 A1 | 10/2001 |
| DE | 101 21 210 A1 | 11/2002 |
| DE | 19546692 C2 | 11/2002 |
| DE | 10301026 A1 | 2/2004 |
| DE | 10302447 A1 | 7/2004 |
| DE | 10335948 B3 | 2/2005 |
| DE | 10010074 B4 | 4/2005 |
| DE | 19857887 B4 | 5/2005 |
| DE | 10010073 B4 | 12/2005 |
| DE | 102005051849 A1 | 5/2007 |
| EP | 0084395 A1 | 7/1983 |
| EP | 0458877 | 8/1990 |
| EP | 0402036 B1 | 12/1990 |
| EP | 0402176 B1 | 12/1990 |
| EP | 0458877 B1 | 4/1991 |
| EP | 0515324 A1 | 11/1992 |
| EP | 0547135 B1 | 6/1993 |
| EP | 0871414 | 9/1995 |
| EP | 0 592 410 B1 | 10/1995 |
| EP | 0756498 | 10/1995 |
| EP | 0 592 410 B1 | 11/1995 |
| EP | 0786970 | 5/1996 |
| EP | 0729364 B1 | 9/1996 |
| EP | 0756498 B1 | 5/1997 |
| EP | 0778775 B1 | 6/1997 |
| EP | 0786970 | 8/1997 |
| EP | 0888142 | 9/1997 |
| EP | 0971649 | 10/1998 |
| EP | 0928615 A1 | 7/1999 |
| EP | 1051204 | 7/1999 |
| EP | 1089676 | 12/1999 |
| EP | 0986348 B1 | 3/2000 |
| EP | 1117446 | 4/2000 |
| EP | 1 164 976 | 8/2000 |
| EP | 1158937 | 9/2000 |
| EP | 1 251 805 B1 | 10/2000 |
| EP | 1041942 B1 | 10/2000 |
| EP | 1041943 B1 | 10/2000 |
| EP | 1171061 | 10/2000 |
| EP | 1206179 | 2/2001 |
| EP | 1 233 731 | 5/2001 |
| EP | 1117446 B1 | 7/2001 |
| EP | 1 255 510 | 8/2001 |
| EP | 1259193 | 9/2001 |
| EP | 1 233 731 B1 | 5/2002 |
| EP | 1 330 213 | 5/2002 |
| EP | 1206179 B1 | 5/2002 |
| EP | 1347785 | 8/2002 |
| EP | 1235537 | 9/2002 |
| EP | 1248655 | 10/2002 |
| EP | 1251804 B1 | 10/2002 |
| EP | 1257305 | 11/2002 |
| EP | 0 971 649 B1 | 12/2002 |
| EP | 1395208 | 12/2002 |
| EP | 1 401 359 | 1/2003 |
| EP | 1406561 | 1/2003 |
| EP | 1281357 A2 | 2/2003 |

| | | |
|---|---|---|
| EP | 1281375 A2 | 2/2003 |
| EP | 1408882 | 2/2003 |
| EP | 1 435 878 | 4/2003 |
| EP | 1 435 879 | 4/2003 |
| EP | 1 441 672 | 6/2003 |
| EP | 1 017 868 B1 | 9/2003 |
| EP | 1354569 A1 | 10/2003 |
| EP | 1494616 | 10/2003 |
| EP | 1 519 697 | 1/2004 |
| EP | 1 539 047 | 4/2004 |
| EP | 1551274 | 4/2004 |
| EP | 1 560 542 | 5/2004 |
| EP | 1414295 | 5/2004 |
| EP | 1 603 493 | 9/2004 |
| EP | 1452153 A1 | 9/2004 |
| EP | 0987998 B1 | 10/2004 |
| EP | 1 087 727 B1 | 11/2004 |
| EP | 1499366 B1 | 1/2005 |
| EP | 1 663 070 | 3/2005 |
| EP | 1518518 A2 | 3/2005 |
| EP | 1 253 875 B1 | 4/2005 |
| EP | 1 667 614 | 4/2005 |
| EP | 1 251 803 B1 | 6/2005 |
| EP | 1 702 247 | 7/2005 |
| EP | 1734902 | 8/2005 |
| EP | 1469797 B1 | 11/2005 |
| EP | 1835948 | 6/2006 |
| EP | 1863545 | 9/2006 |
| EP | 1893132 | 11/2006 |
| EP | 1901681 | 12/2006 |
| EP | 1 255 510 B1 | 3/2007 |
| EP | 1835948 | 9/2007 |
| EP | 1112042 B1 | 11/2007 |
| EP | 1878407 A1 | 1/2008 |
| EP | 1886649 A2 | 2/2008 |
| EP | 1 900 343 A2 | 3/2008 |
| EP | 1259195 B1 | 10/2008 |
| EP | 2 000 115 A2 | 12/2008 |
| FR | 2 788 217 A | 7/2000 |
| FR | 2 815 844 A1 | 5/2002 |
| FR | 2828263 A1 | 2/2003 |
| GB | 2433700 A | 7/2007 |
| GB | 2440809 A | 2/2008 |
| JP | 2003-523262 | 8/2003 |
| JP | 2003-524504 | 8/2003 |
| JP | 2005-118585 | 5/2005 |
| JP | 2007-296375 | 11/2007 |
| WO | WO-90/09102 | 8/1990 |
| WO | WO-95/24873 | 9/1995 |
| WO | WO-95/28183 | 10/1995 |
| WO | WO-96/13227 | 5/1996 |
| WO | WO-97/32615 | 9/1997 |
| WO | WO-98/43556 | 10/1998 |
| WO | WO-98/46165 | 10/1998 |
| WO | WO-99/37337 | 7/1999 |
| WO | WO-99/66863 | 12/1999 |
| WO | WO 00/15148 | 3/2000 |
| WO | WO-00/18445 | 4/2000 |
| WO | WO 00/25702 A1 | 5/2000 |
| WO | WO 00/41652 | 7/2000 |
| WO | WO 00/47139 A1 | 8/2000 |
| WO | WO-00/53125 | 9/2000 |
| WO | WO-00/62714 | 10/2000 |
| WO | WO-01/10209 A1 | 2/2001 |
| WO | WO 01/35870 A1 | 5/2001 |
| WO | WO-01/41679 A1 | 6/2001 |
| WO | WO-01/51104 A1 | 7/2001 |
| WO | WO 01/54625 A1 | 8/2001 |
| WO | WO-01/58503 A1 | 8/2001 |
| WO | WO 01/62189 A1 | 8/2001 |
| WO | WO 01/64137 A1 | 9/2001 |
| WO | WO 02/22054 A1 | 3/2002 |
| WO | WO 02/36048 A1 | 5/2002 |
| WO | WO-02/058745 A1 | 8/2002 |
| WO | WO-02/100301 A1 | 12/2002 |
| WO | WO-02/102286 A1 | 12/2002 |
| WO | WO 03/003949 A2 | 1/2003 |
| WO | WO-03/007795 A1 | 1/2003 |
| WO | WO-03/009785 A1 | 2/2003 |
| WO | WO 03/011195 A2 | 2/2003 |
| WO | WO 03/013239 | 2/2003 |
| WO | WO 03/028592 A1 | 4/2003 |
| WO | WO 03/047468 A1 | 6/2003 |
| WO | WO-03/079928 A2 | 10/2003 |
| WO | WO 03/096935 A1 | 11/2003 |
| WO | WO 2004/004597 A2 | 1/2004 |
| WO | WO 2004/016200 A1 | 2/2004 |
| WO | WO 2004/016201 A2 | 2/2004 |
| WO | WO 2004/019825 A1 | 3/2004 |
| WO | WO-2004/026117 A2 | 4/2004 |
| WO | WO 2004/026173 A2 | 4/2004 |
| WO | WO 2004/043301 A1 | 5/2004 |
| WO | WO 2004/064671 A2 | 8/2004 |
| WO | WO 2004/082527 A2 | 9/2004 |
| WO | WO 2004/096100 A1 | 11/2004 |
| WO | WO 2005/021063 A2 | 3/2005 |
| WO | WO 2005/034812 A1 | 4/2005 |
| WO | WO 2005/063980 A1 | 7/2005 |
| WO | WO-2005/072654 A1 | 8/2005 |
| WO | WO 2006/066327 | 6/2006 |
| WO | WO-2006/066327 A1 | 6/2006 |
| WO | WO 2006/076890 A1 | 7/2006 |
| WO | WO-2006/102063 A2 | 9/2006 |
| WO | WO 2006/108090 A2 | 10/2006 |
| WO | WO 2006/124649 A2 | 11/2006 |
| WO | WO 2006/127756 A2 | 11/2006 |
| WO | WO 2006/127765 A1 | 11/2006 |
| WO | WO-2006/132948 A1 | 12/2006 |
| WO | WO 2007/047488 A2 | 4/2007 |
| WO | WO 2007/047945 A2 | 4/2007 |
| WO | WO 2007/048529 A1 | 5/2007 |
| WO | WO 2007/059252 A1 | 5/2007 |
| WO | WO-2007/071436 A2 | 6/2007 |
| WO | WO 2007/120543 A1 | 10/2007 |
| WO | WO-2008/028569 A1 | 3/2008 |
| WO | WO 2008/045949 | 4/2008 |
| WO | WO 2008/070797 A2 | 6/2008 |
| WO | WO 2006/076890 | 7/2008 |
| WO | WO 2008/079962 A1 | 7/2008 |
| WO | WO 2008/101083 A2 | 8/2008 |

OTHER PUBLICATIONS

International Search Report for PCT/EP2006/010519.
Aortenklappenbioprothese erfolgreich in der Entwicklung, (1 page) May 16, 2003.
Translation of Aortenklappenbioprothese erfolgreich in der Entwicklung (2 pages).
Screen shots from http://www.fraunhofer.de/presse/filme/2006/index.jsp (2 pages), 2006.
Liang, Ma, et al., "Double-crowned valved stents for off-pump mitral valve replacement," European Journal of Cardio-Thoracic Surgery, 194-198 (5 pages), Jun. 13, 2005.
Huber, Christoph, et al. "Direct Access Valve Replacement (DAVR)—are we entering a new era in cardiac surgery?" European Journal of Cardio-Thoracic Surgery, 380-385, (6 pages), Jan. 19, 2006.
Translation of DE 19546692 A1 (4 pages).
Translation of EP 1469797 B1 (16 pages).
Translation of DE 198 57 887 B4 (11 pages).

* cited by examiner

SELF-EXPANDABLE MEDICAL INSTRUMENT FOR TREATING DEFECTS IN A PATIENT'S HEART

CROSS-REFERENCE TO RELATED APPLICATIONS

The present application claims priority from German Patent Application No. DE 10 2005 052 628.4, which was filed on Nov. 4, 2005, by Hans-Reiner Figulla et al. for a SELF-EXPANDABLE MEDICAL INSTRUMENT FOR TREATING DEFECTS IN A PATIENT'S HEART and is hereby incorporated by reference.

BACKGROUND OF THE INVENTION

1. Field of the Invention

The present invention relates to a self-expandable medical instrument for treating defects in a patient's heart, in particular for the transvascular implantation of a prosthetic heart valve, whereby the medical instrument can be introduced via a catheter system into the patient's body in a minimally-invasive procedure. In particular, the invention relates to a device for the transvascular replacement of diseased heart valves.

2. Background Information

A device of this type is known in principle to medical technology. At present, biological or mechanical valve models are available to substitute for human heart valves which are usually fixedly sewn into the bed of the heart valve during a surgical procedure through an opening in the thorax after removal of the diseased heart valve. In this surgical procedure, the patient's circulation must be maintained by a heart-lung machine, whereby cardiac arrest is induced during the implantation of the prosthetic heart valve. This consequently makes the surgical procedure a risky one coupled with the associated risks for the patients and a lengthy post-operative treatment phase. In particular, the risks of such a surgical procedure are often no longer justifiable in the case of multi-morbid patients.

Minimally-invasive treatment procedures of recent development are characterized in particular by the surgery being able to be performed under local anesthesia. One approach provides for implanting a self-expanding stent connected to a collapsible heart valve into the human body by means of an appropriate catheter system. The catheter systems is used to guide such a self-expanding prosthetic heart valve through the inguinal artery or vein to its site of implantation at the heart. After reaching the site of implantation, the stent, consisting for example of a plurality of self-expanding stent segments which can be bent relative one another in its longitudinal direction, can then be successively expanded. Following this expansion, anchoring hooks can for example support the anchoring of the prosthetic heart valve at least in the respective blood vessel close to the heart. The actual prosthetic heart valve itself is thereby in the direct proximal area of the stent.

Known for example from the DE 100 10 074 A1 printed publication is a device for fastening and anchoring prosthetic heart valves, which is essentially formed from wire-shaped interconnected elements. The device thereby provides for using various different arched elements in order to attain a secure fixation of and support for the prosthetic heart valve. To this end, the device described in this printed publication makes use of three identical pairs of arched elements, arranged to be offset from one another by 120°. These arched elements are interconnected by means of solid articulations, whereby the solid articulations fulfill the function of pivot bearings. Additional arched elements bent opposite to each other are furthermore provided which form rocker arms as equal in length as possible in order to achieve a secure placement of the arched elements even when subject to peristaltic actions on the heart and blood vessels and a solid sealing for an implanted and anchored prosthetic heart valve.

In the known solutions, however, there is a risk of heart valve implant malalignment. This essentially relates to the exact positioning and longitudinal orientation of the prosthetic heart valve to be implanted. In particular, it is only with immense skill on the part of the attending surgeon—if at all—that a stent with the prosthetic heart valve at its proximal end winds up being positioned so precisely in the proximity of the patient's diseased heart valve that both sufficient lateral positioning accuracy as well as a suitable longitudinal placement to the prosthetic heart valve can be optimally ensured.

Among other complications, an implantation malalignment of a less than optimally positioned prosthetic heart valve can lead to, for example, leakage or valvular regurgitation, which puts a substantial burden on the ventricle. Should, for example, a prosthetic heart valve be implanted too far above the actual heart valve plane, this can lead to occlusion of the coronary artery origination (coronaries) and thus to a fatal coronary ischemia with myocardial infarction. It is therefore imperative for an implanted prosthetic heart valve to meet all the respective requirements for both the accuracy of the lateral positioning as well as the longitudinal placement.

In conventional implantation techniques in which self-expandable prosthetic heart valves are, for example, guided through a patient's inguinal artery to the site of deployment at the heart in a minimally-invasive procedure, the prosthesis is usually introduced using a guide wire and catheters, whereby conventional balloon catheters can also be used. Although such a surgical introduction can be monitored and controlled, for example with fluoroscopy (Cardiac Catheterization Laboratory=CCL) or with ultrasound (Transesophageal Echocardiogram=TEE), oftentimes—due to the limited maneuverability of the prosthetic heart valve which is still in a collapsed state during the introduction procedure and despite being in the collapsed state is still of relatively large size—it is not possible to ensure the required positioning accuracy and especially the longitudinal placement to the prosthetic heart valve implant with the corresponding anchoring elements affixed thereto. In particular—as a result of a possible coronary artery occlusion—an angle misalignment to the implanted prosthetic heart valve from the optimum site of deployment can pose a threat to the respective patient.

In designing a prosthetic heart valve, special consideration must in particular be given to the substantial forces also acting on the prosthetic during the filling period of the cardiac cycle (diastole), necessitating a secure anchorage in order to prevent the implanted prosthetic heart valve from dislodging.

Hence on the one hand, the prosthetic heart valve must be able to be maneuvered to the greatest extent possible in the respective coronary artery during the implantation procedure so as to ensure optimum positioning accuracy and, on the other hand, the implanted prosthesis must be able to be firmly anchored at its site of implantation in order to effectively prevent subsequent prosthesis misalignment.

The present invention addresses the problem that the known devices for transvascular implantation and fixation of prosthetic heart valves are often not suitable for a simple implantation of a prosthetic heart valve with the required positioning accuracy. Moreover, explanting a previously implanted prosthetic heart valve in a minimally-invasive procedure or accordingly correcting an incorrectly positioned prosthetic heart valve has to date often only been possible with great effort, if at all.

On the basis of the problems as set forth, one task on which the present invention is based is that of providing a device for the transvascular implantation and fixation of prosthetic heart valves which remedies the above-described disadvantages inherent to conventional implantation systems.

SUMMARY OF THE INVENTION

According to the invention, this task is solved by a medical self-expandable instrument for treating heart defects in a patient, in particular for the transvascular implantation of a prosthetic heart valve, whereby the medical instrument can be introduced into the patient's body in a minimally-invasive procedure using a catheter system and a stent made from a flexible mesh of thin wires or filaments. It is thereby provided for the stent or the mesh to exhibit a first predefinable shape while the medical instrument is being inserted into the patient's body and a second predefinable shape when the medical instrument is in its implanted state, whereby the medical instrument is in a collapsed state in the first shape of the stent or mesh and in an expanded state in the second shape of the stent or mesh. In particular, in its expanded state, the medical instrument according to the inventive solution exhibits a distal retention area with a laterally-inverted beaded portion, which in the implanted state of the medical instrument is engageable with at least one pocket of the patient's defective heart valve, a proximal retention area, as well as a center area positioned between the distal and the proximal retention area. In its expanded state, the center area of the medical instrument thereby exhibits a smaller diameter than the proximal and/or distal retention area, whereby in the implanted state of the medical instrument at the height of the patient's defective heart valve, the center area is designed to form a positive connection with the vascular wall at or in the direct proximity of the defective heart valve.

The advantages of the invention are in particular noted to be in the providing of a transvascularly introducible medical instrument, in particular for treating a patient's heart defects, whereby the medical instrument is suitable to be delivered by catheter to the is defect to be treated in the patient's heart. Because the medical instrument is configured as a self-expandable instrument and essentially consists of a stent made of a flexible mesh of thin wires or filaments, one particularly advantageous result achieved is that the medical instrument—regardless of the size of the heart valve to be treated and regardless of the diameter to the defective heart valve— can self-adapt to the defective heart valve, and in such a way that, on the one hand, the portions of the medical instrument protruding into the bloodstream flowing past the implanted medical instrument are as small as possible, while at the same time, an optimal positioning, secure anchorage and optimal lateral sealing of the implanted medical instrument is ensured.

Accordingly, the medical instrument is optimally positionable at the defective heart valve and anchored there in extremely stable manner, whereby at the same time, embolism-related problems can be prevented. Using thin wires or filaments as the source material of the stent or the medical instrument according to the invention respectively yields the further advantage of the medical instrument exhibiting long-term mechanical stability. This thus sustainably prevents structural fractures from occurring in the instrument employed. The mesh furthermore has sufficient rigidity.

Briefly summarized, the solution according to the invention is characterized by the medical instrument comprising a stent made from a flexible mesh, in particular a wire mesh, which upon release from the catheter inverts in mushroom-shape form into the pockets of the diseased heart valve and is clamped there by this inversion. This thus provides an optimum positioning and stable anchoring of a prosthetic heart valve disposed or provided in the middle of the stent. At the same time, an optimum lateral sealing of the implanted prosthetic valve is ensured.

Preferred embodiments of the medical instrument are indicated in the subclaims.

A particularly preferred realization of the medical instrument according to the invention accordingly provides for the stent to furthermore exhibit a self-expandable prosthetic heart valve arranged in the center area which self-expands upon the medical instrument being released from the catheter system and which then assumes the function of the patient's defective heart valve. In this preferred embodiment, the mesh thus serves the medical instrument as a heart valve stent in the anchoring and positioning of the prosthetic heart valve arranged in the center area of the medical instrument. The medical instrument is in particular characterized by the fact that, due to its shape in the expanded state, it not only provides an extremely stable anchoring of the prosthetic heart valve, but also a self-positioning of same at the height of the defective heart valve to be replaced.

With respect to the mesh which forms the prosthetic heart valve stent, it is preferably provided for same to be a mesh tube such that the medical instrument exhibits a form open to the proximal and distal end in its expanded state. A mesh tube offers the advantage of blood being able to flow through the medical instrument in the implanted state of the expanded medical instrument, whereby—except for the prosthetic heart valve disposed in the center area of the medical instrument— virtually no foreign components protrude into the bloodstream.

It is furthermore conceivable for the beaded portion at the distal retention area of the stent in the expanded medical instrument to be formed by the mushroom-shaped outwardly turned-back distal end of the mesh. In particular, the beaded portion at the distal retention area of the expanded medical instrument in the implanted state of the medical instrument is thereby invertible in the at least one pocket of the patient's defective heart valve and thus serves as a self-positioning means for positioning the medical instrument at the height of the patient's defective heart valve.

According to a further aspect of the present invention, because of the self-expanding properties of the stent made from the flexible mesh, the proximal retention area of the stent forms a force-fit connection with the vascular wall when the medical instrument is in its expanded state, thus ensuring a stable anchoring of the implanted medical instrument.

On the other hand, the center area of the stent in the expanded medical instrument is advantageously configured such that based on the self-expanding properties of the stent made from the flexible mesh, the center area presses the patient's defective heart valve against the vascular wall distal the defective heart valve in the implanted state of the medical instrument.

With respect to the shape of the medical instrument in its expanded state, the stent in its second shape respectively, it is preferable for same to be of a shape similar to a barbell, whereby both the distal as well as the proximal retention area are respectively configured in the shape of a mushroom cap. It is furthermore preferred for the center area of the stent to exhibit a smaller diameter in the expanded medical instrument compared to the proximal and distal retention areas, whereby the center area exhibits a length which corresponds approximately to the length of the defective heart valve.

It is particularly preferred for the mesh-based stent having a self-expandable prosthetic heart valve arranged at its center area to taper to the diameter of the catheter system used in the transvascular surgical procedure.

In order to allow for a medical instrument already implanted into the body of the patient being able to be subsequently explanted, a preferred further development of the solution according to the invention provides for the stent to exhibit a mounting engageable with an explantation catheter system on its proximal and/or distal end, wherein the medical instrument is moreover configured such that an external manipulation will effect its alteration from the expanded state to its collapsed state so that the medical instrument, the stent with the prosthetic heart valve respectively, will be as simple as possible to explant.

A further aspect of the invention provides for the flexible mesh forming the stent for the self-expandable medical instrument to have a multi-layered configuration around the patient's defective heart valve in the implanted state of the medical instrument.

Because a stent formed from a flexible mesh is used and because of the self-expanding properties to the medical instrument thus attained, it is particularly preferable for the stent with the self-expandable prosthetic heart valve arranged at its center area to be configured such that in the implanted state of the expanded medical instrument, the second shape of the stent, and thus the medical instrument, adapts to the anatomical conditions in such a manner that the prosthetic heart valve attains a maximum expansion on the one hand and, on the other, an optimum lateral sealing to the vascular wall is provided.

It is of particular advantage for the stent made of flexible mesh, in particular wire mesh, with a self-expanding prosthetic heart valve arranged in its center area to be configured such that the stent with the prosthetic heart valve can be withdrawn back into the catheter system, and thus removable from the patient's body, at any time during the implantation of the medical instrument.

It is provided for the flexible mesh to be made from nitinol or another material having shape-memory or memory effect. Other applicable materials would include, for example, copper/zinc/aluminum alloys, gold/cadmium alloys or also iron-based alloys such as, for example, iron/manganese, silicon alloys, as well as also plastics, which are all characterized by the fact that they have extremely high memory capabilities.

Lastly, with regard to the use of the medical instrument, it is particularly preferred for the flexible stent of mesh with the prosthetic heart valve at its center area to be used not only for replacing aorta valves but also mitral, pulmonary and tricuspid valves.

BRIEF DESCRIPTION OF THE DRAWINGS

The following will make reference to the accompanying figures in describing the invention in greater detail, wherein the figures are as follows.

DETAILED DESCRIPTION OF AN ILLUSTRATIVE EMBODIMENT

The embodiment depicted in the figures of the inventive self-expandable medical instrument 100 for treating defects of a patient's heart relates to a self-expandable medical instrument for the transvascular implantation of a prosthetic heart valve 30, wherein the medical instrument 100 can be introduced into a patient's body in minimally-invasive fashion by means of a catheter system 40 and consists of a stent 1 made from a flexible mesh (2) of thin wires or filaments 2'.

Figure 1:
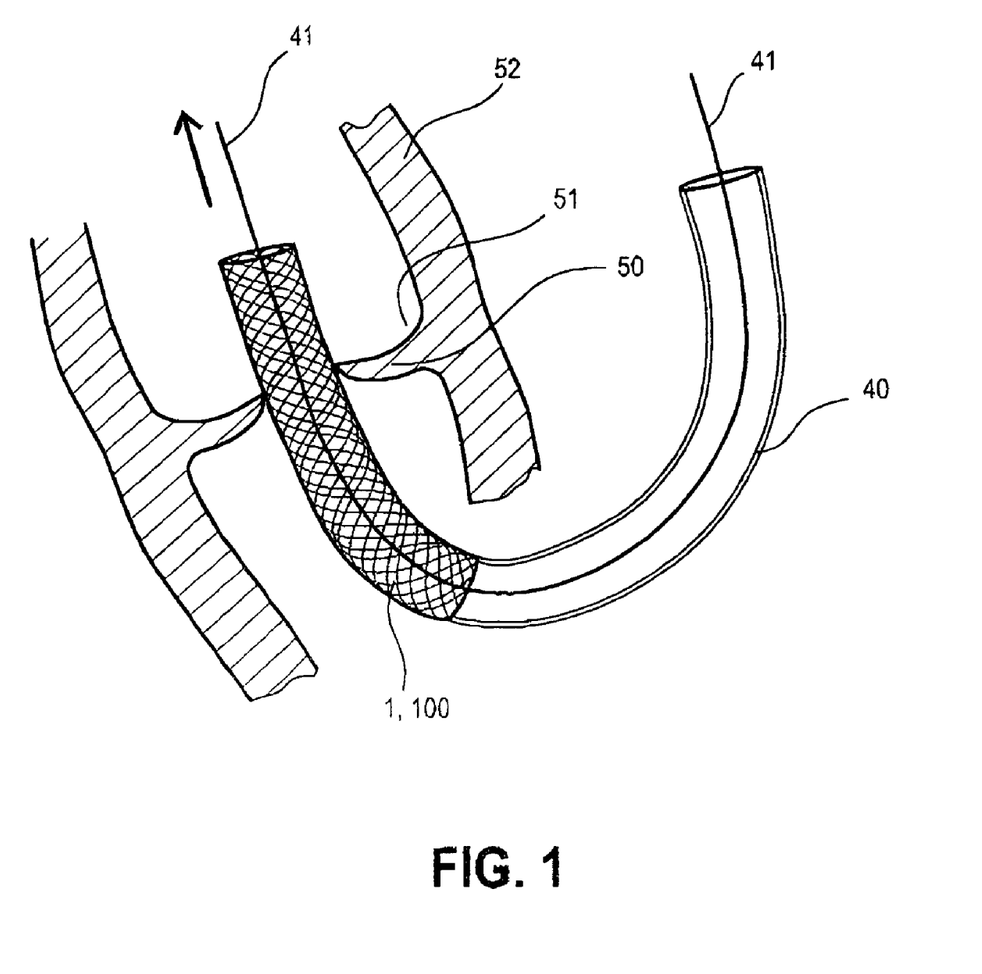
FIG. 1 shows a preferred embodiment of the medical insturrment according to the invention during insertion into the body of a patient, whereby the flexible mesh, which here forms the aorta valve stent, exhibits its first predefined shape.

As FIG. 1 shows, the stent 1 configured from flexible mesh 2 is in a first predefined shape during the insertion of the medical instrument 100 into the patient's body. The stent 1 further exhibits a self-expandable prosthetic heart valve 30 at its center area 15, which is covered by mesh 2 in FIG. 1 and thus not explicitly shown. As will be described below, the self-expandable prosthetic heart valve 30 unfolds by itself upon the medical instrument 100, the stent 1 respectively, being released from the catheter system 40.

What can in particular be noted from FIG. 1 is that the stent 1 configured from mesh 2 with the prosthetic heart valve 30 arranged at its center area 15 (not explicitly shown in FIG. 1) tapers to the diameter of the catheter system 40 used for the transvascular procedure. In this state, the medical instrument 100 is seen as being in its collapsed state.

FIG. 1 specifically depicts a state immediately prior to the medical instrument 100 in its collapsed state being brought through the defective aorta valve 50 of the patient to the ascending aorta by means of a guide wire 41, and after the medical instrument 100 having been transseptally inserted into the left ventricle by an insertion catheter system 40. As already indicated, only the flexible mesh 2 can be recognized in the depiction of the medical instrument 100 shown in the FIG. 1 representation, same assuming the function of the aorta valve stent 1 and with the (not explicitly depicted) collapsed prosthetic heart valve 50 disposed at its center area 15.

Figure 2:
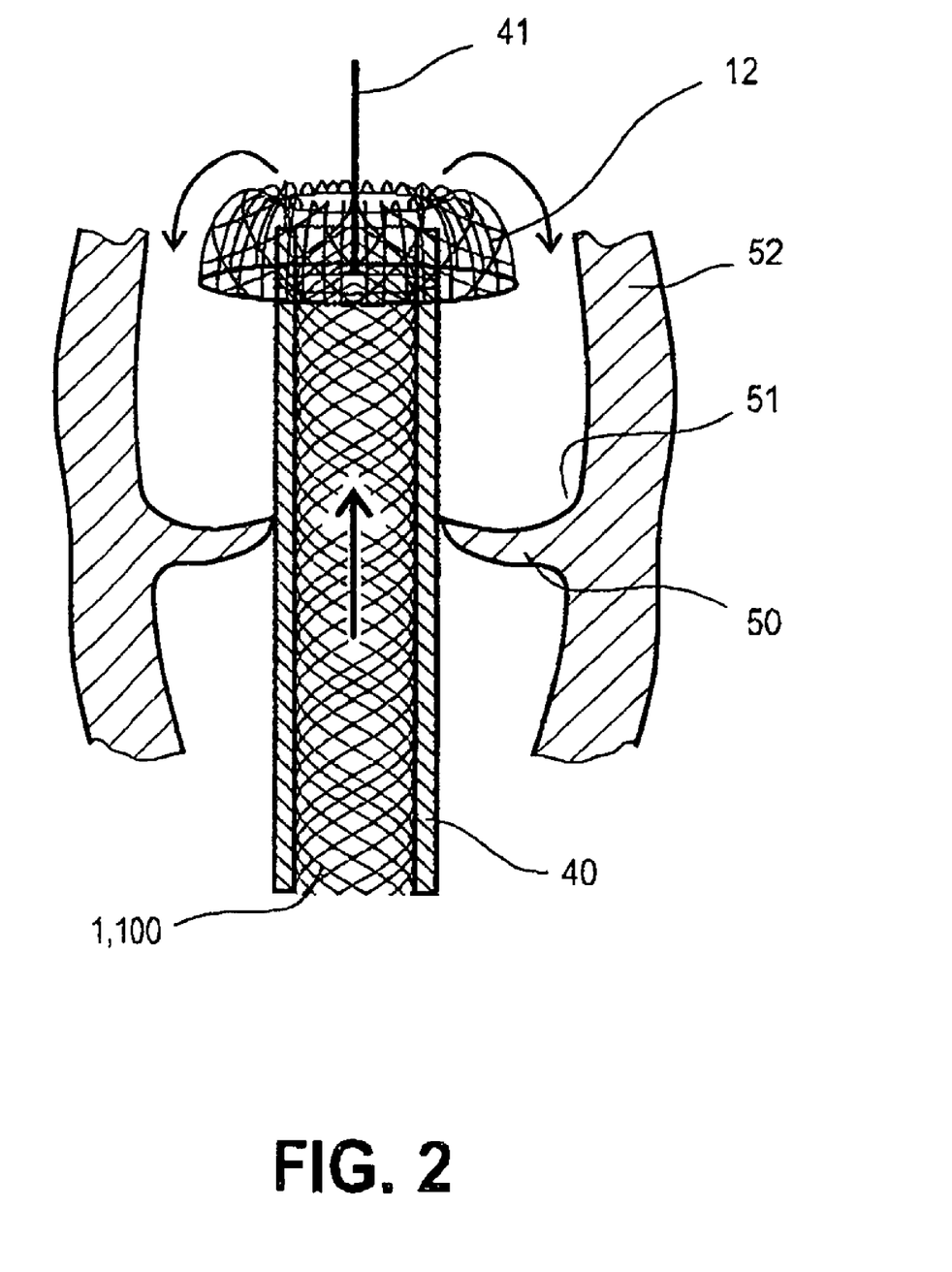
FIG. 2 shows the medical instrument of FIG. 1 in a first state in which the aorta valve stent is released from the insertion catheter system.

FIG. 2 shows a state in which—starting from the position shown in FIG. 1—the first portion of the inner wire mesh 2 of stent 1 is mushroomed out of the corresponding insertion catheter system 40, whereby this portion forms the beaded portion 12 at the distal retention area 10 of the stent in the fully expanded state of medical instrument 100, arching laterally in a mushroom shape. In the implanted state of medical instrument 100, the laterally outward capping beaded portion 12 engages in at least one pocket 51 of the patient's defective heart valve 50, as will be described in detail below.

Figure 3:
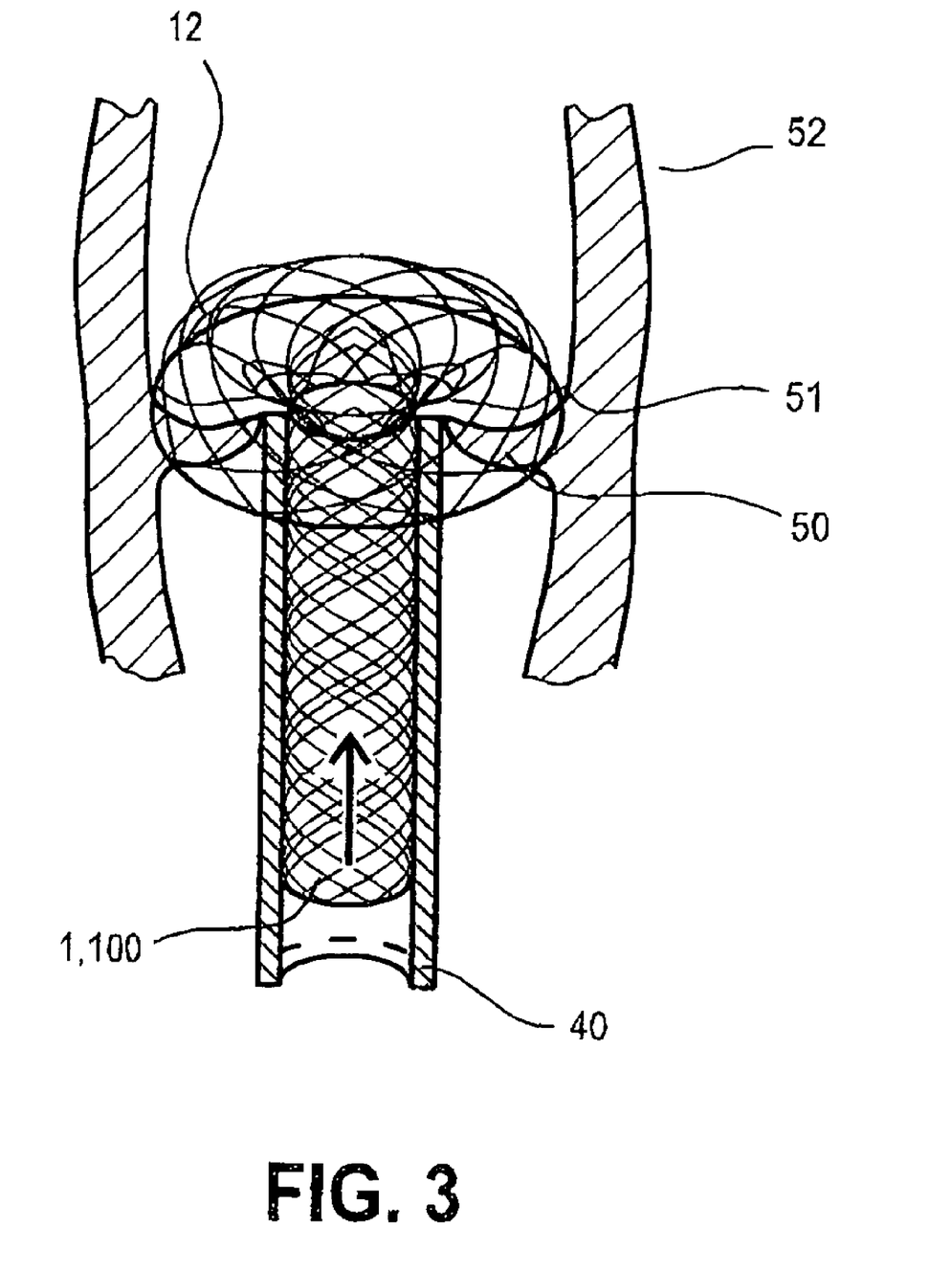
FIG. 3 shows the medical instrument of FIG. 2 in a further second state during the release of the aorta valve stent from the insertion catheter system.

FIG. 3 shows a further state in which the entire stent 1 is drawn back to the height of the defective aorta valve 50, where the defective valve 50 is hooked in form-fit manner to the "midriff" of stent 1; i.e., the center area 15 of the doublemushroomed stent 1 after full expansion, after the distal (upper) portion of the wire mesh 2 inverts into place and the beaded portion 12 is fully formed.

Figure 4:
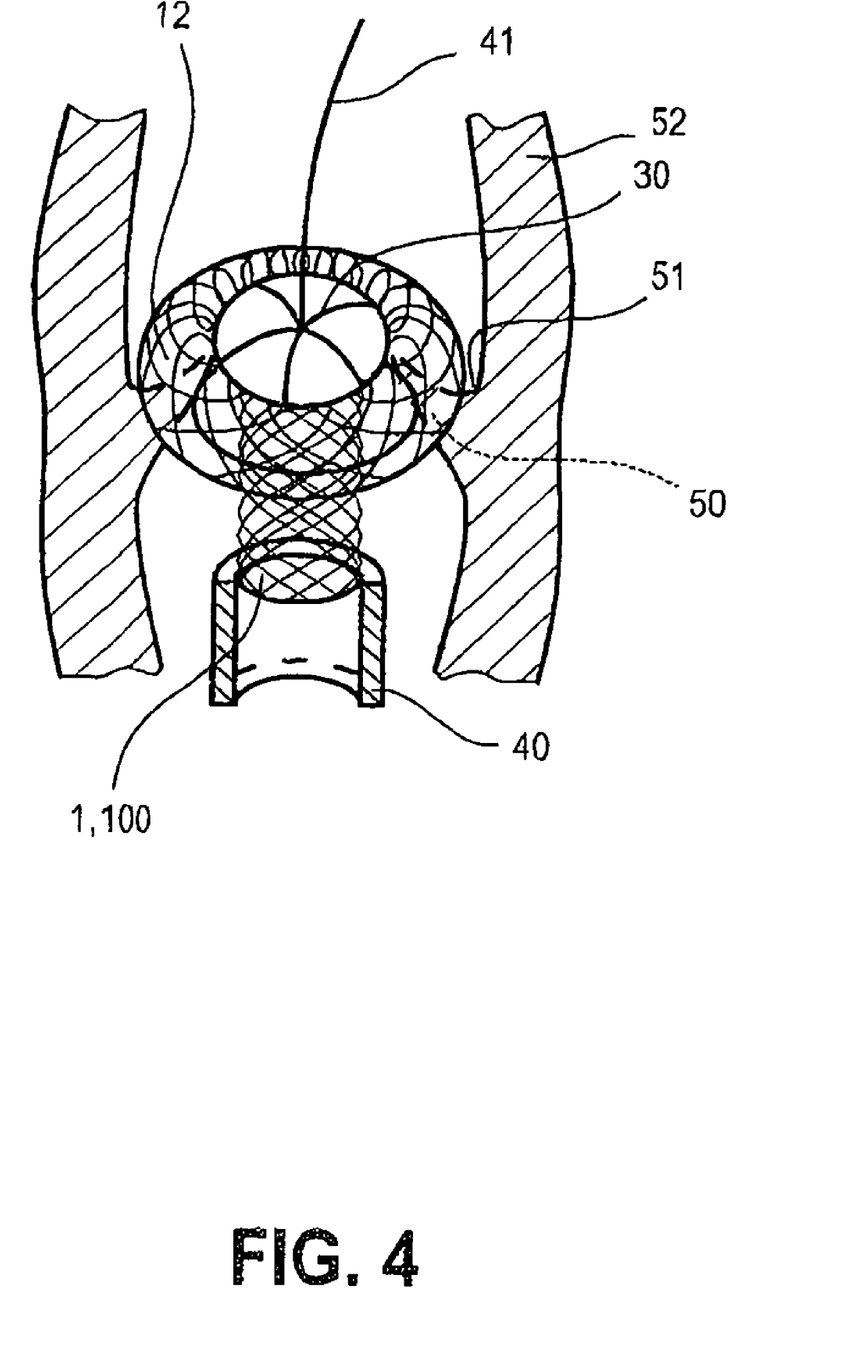
FIG. 4 shows the medical instrument of FIG. 3 in a further advanced third state during the release of the aorta valve stent from the insertion catheter system.

FIG. 4 meanwhile shows a state in which by the further extending of stent 1 formed from the mesh 2 out of the catheter system 40, the self-expandable prosthetic heart valve 30 disposed in the center area 15 within stent 1 emerges. In this state, the patient's defective (old) valve 50 engages with the midsectioned center area 15 of stent 1. The beaded portion 12 at the distal retention area 10 of stent 1 is furthermore turned inside out by the mushroom-shaped inverting of the distal end of mesh 2, whereby the beaded portion 12 turns to fit into the pockets 51 of the patient's defective heart valve 50 so as to serve as a means for positioning the medical instrument 100 at the height of the patient's defective heart valve 50.

Upon stent 1 being further extended from the catheter system 40, the proximal retention area 20 of stent 1 finally unfolds, whereby same then forms a force-fit connection with the vascular wall 52 in the direct proximity of the defective heart valve 50 due to the self-expanding properties of the mesh 2. At the same time, the center area 15 of stent 1 presses against the aorta wall 52, whereby the self-expandable mesh 2 expands further, thereby clamping the prosthetic valve 30.

Figure 5A:
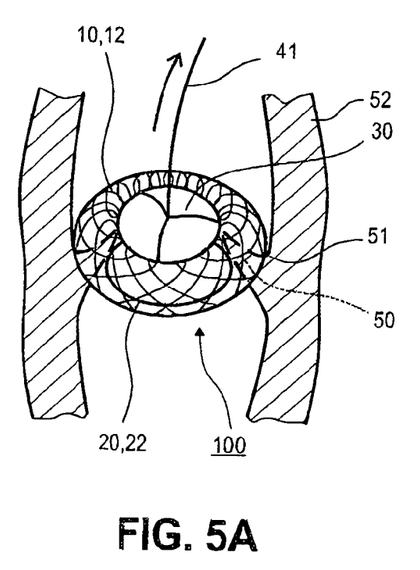
FIG. 5 shows a state in which the aorta valve stent and thus the medical instrument according to FIGS. 1 to 4 is fully expanded and implanted at the height of the patient's heart valve.
Figure 5B:
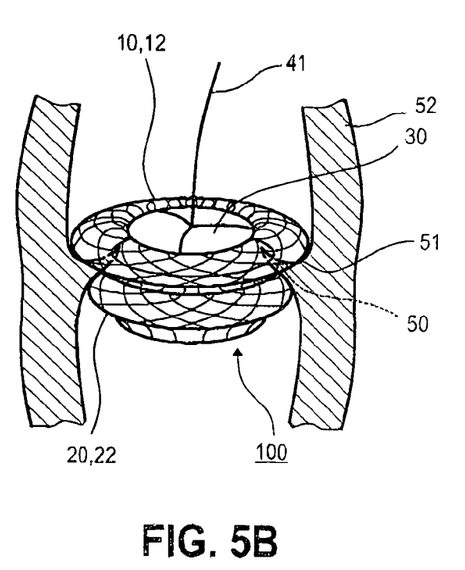

Both FIG. 5a and FIG. 5b show a state in which the mechanical prosthetic heart valve 30 is correctly positioned and fully closed, whereby the defective (old) valve 50 remains in the heart and is pressed against the vascular wall 52. Moreover indicated is how, following a check of the proper seating and the error-free functioning of the mechanical prosthetic heart valve 30, the guide wire 41 can then be removed again. It is hereby pointed out that in the event of valve malfunction, the guide wire 41 can retract stent 1 with the integrated prosthetic heart valve 30 back into the insertion catheter system as necessary and the stent can be replaced by another stent with an integrated prosthetic heart valve.

Figure 6:
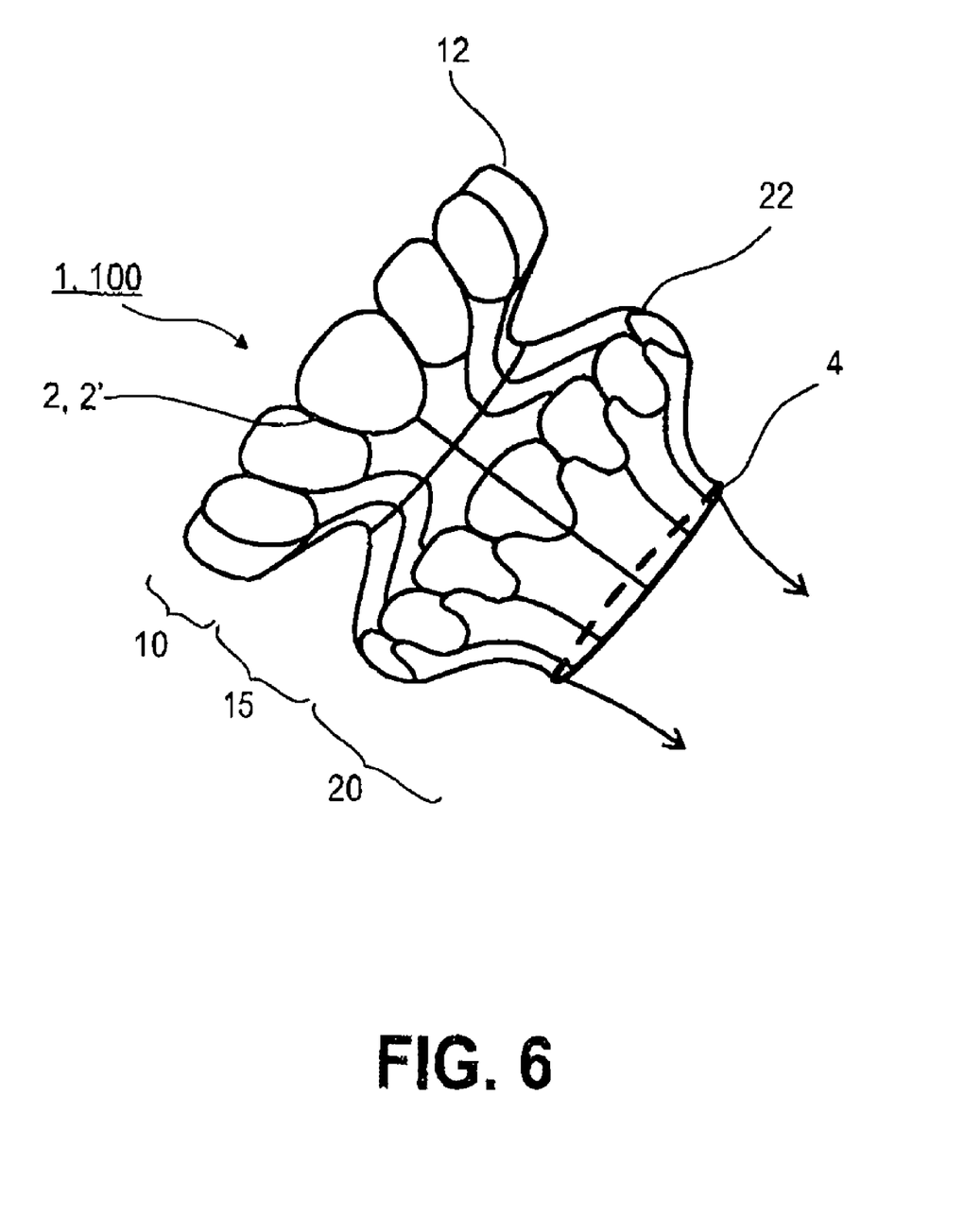
FIG. 6 shows a perspective view of the expanded medical instrument according to the preferred embodiment.

FIG. 6 shows a perspective view of the expanded medical instrument 100 in accordance with the preferred embodiment. It can be recognized that in the expanded state of medical instrument 100, the stent 1 exhibits a barbell-like shape, whereby the stent 1 formed from the flexible mesh 2 with the self-expandable prosthetic heart valve 30 disposed within the center area 15 of stent 1 (not recognizable in FIG. 6) is configured such that the second shape of stent 1 in the implanted state of the expanded medical instrument 100 can adapt to the anatomical conditions in such a manner that the prosthetic heart valve 30 attains maximum expansion on the one hand and, on the other, achieves an optimum lateral sealing to vascular wall 52.

It can further be noted from FIG. 6 that in the expanded state of medical instrument 100, the center area 15 of stent 1 exhibits a smaller diameter than the proximal and distal retention areas 10 and 20, whereby the center area 15 exhibits a length which corresponds approximately to the length of the defective heart valve 50.

The embodiment of the medical instrument 100 as depicted moreover provides for the stent 1 to have a mounting 4 in the form of a ring at its proximal end which can be brought into engagement with a (not shown) explantation catheter system, whereby the medical instrument 100 is configured such that external manipulation can commute it from its expanded state into its collapsed state.

Figure 7:
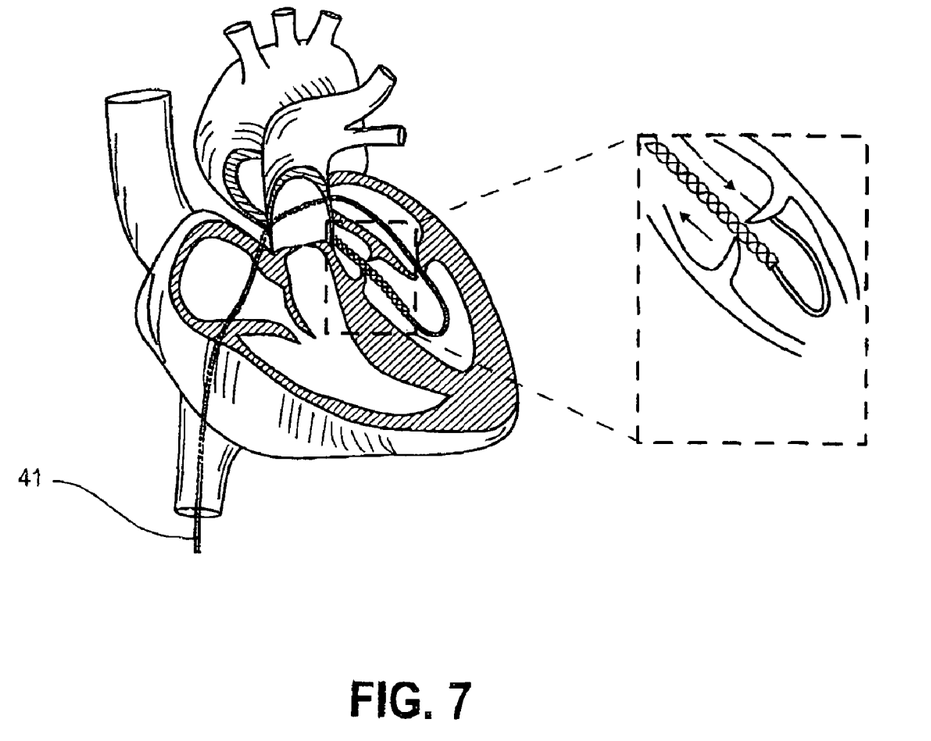
FIG. 7 shows a conceivable route of implantation for the medical instrument according to the preferred embodiment.

FIG. 7 shows how a guide wire 41 can be fed through the vena cava to the right atrium and the interatrial septum in the left atrium and further into the left ventricle and from there through the left ventricular outflow tract and the aorta valve to the ascending aorta.

It is particularly preferred for the transvascular replacement of a patient's defective aorta valve 50, for example, to sew or otherwise fasten a suitable prosthetic valve 30 in the middle of the center area 15 of the stent 1 configured from flexible mesh 2. The stent 1 with the integrated prosthetic valve 30 can then be tapered to the diameter of the catheter system 40 used in the transvascular surgical procedure and brought through the venous system, passing the interatrial septum, from the right atrium into the left atrium and from there, further into the left ventricle and the left ventricular outflow tract by means of the insertion catheter system.

The stent 1 configured from mesh 2 is released from the insertion catheter system 40 at the height of the defective (old) aorta valve 50, as is shown in FIG. 1. Because stent 1 is discharged successively, at first only the distal retention area 10 is released such that it upends inside out in mushroom shape, as depicted in FIGS. 2 to 4. Subsequent thereto, a careful guiding of the medical instrument 100 toward the ventricles will bring the beaded portion 12 into a form-fit connection in the pockets 51 of the patient's defective old valve 50. The middle midriff, the center area 15 respectively, of stent 1, in which the prosthetic valve 30 is disposed, is now in form-fit seating at the height of the old heart valve (50), as shown in FIG. 4.

The proximal retention area 20 of stent 1 is then also subsequently ejected from the catheter system 40, whereby the artificial prosthetic valve 30 expands and at the same time, the old defective heart valve 50 is pressed against wall 52 due to the self-expanding properties of the wire mesh 2 (cf. FIG. 5). In this state, the beaded or flanged portion 12 at the distal retention area 10 turns inversely outward into the left ventricular outflow tract and thus effects an additional mechanical support and secure anchorage for the medical instrument. In the event of any malfunctioning of stent 1 with the integrated prosthetic valve 30, the guide wire 41 still tethered to stent 1 can effect its removal as necessary, as is indicated in FIGS. 5a and 5b.

It is not imperative to have the route of implantation for the double-mushroom-shaped heart valve stent 1 be transvenous and through the interatrial septum. It is just as conceivable to perform a retrograde implantation procedure through the aortic arch with a catheter system 40 in the manner as described above. The heart valve stent 1 constructed in this manner with its given medial midriff 15 furthermore offers the opportunity of the integrated mounting (ring) of stent 1 subsequently re-fixing onto the integrated prosthetic heart valve 30 and collapsing same by the longitudinal extension of the wire mesh such that it can be removed again through a catheter tube.

The entire detailed route of implantation is depicted in FIG. 7. A guide wire 41 is first introduced through the venous system to the right atrium and through the interatrial septum into the left atrium. From the left atrium, the guide wire is pushed through the left ventricle and the left ventricular outflow tract into the aorta (FIG. 7). Using the guide wire 41 as a rail, the insertion catheter 40 is now advanced into the left ventricular outflow tract and the aortic valve plane. The implantation of the valve as described above now follows.

Alternatively, a guide wire 41 coming from the aortic arch can be pushed in retrograde manner through the aortic valve into the left ventricle. A similar implantation of the aortic valve stent 1 as indicated above is now possible here with a modified catheter tube.

By a design-contingent integration of retaining elements on the self-expandable stent 1, same can also be explanted again with a special catheter subsequent a successful implantation. To this end, the distal or proximal retention area 10, 20 of stent 1 should be drawn by guide wire 41 into a catheter 40 at a plurality of, preferably more than three retaining punctures. In so doing, reversed as in implantation, the mushroom-shaped proximal beaded portion 22 at the proximal retention area 20 of stent 1 is buffeted back, whereby the wire mesh 2 expands again and assumes a state as shown in FIG. 4. Subsequently, the engagement or anchoring of the beaded portion 12 on distal retention area 10 of stent 1 with the pockets 51 of the body's own defective heart valve can be disengaged.

The stent 1 composed of the flexible wire mesh 2 with the prosthetic valve 30 integrated in its center area 15 and adapted to the valve ring and, where necessary, to the outflow tract of the human heart, can be used in similar fashion for replacing mitral valves as well as replacing pulmonary or tricuspid valves.

It is obvious that the following features in particular distinguish the solution according to the invention over the medical instruments as known to date for the transvascular replacement of diseased heart valves:

With the stent configured from the self-expandable mesh with a prosthetic valve disposed in the middle thereof, the old diseased heart valve is enfolded, reversely pushed in and pressed against the vascular wall.

The prosthetic valve in the stent can be implanted both in antegrade (via transseptal puncture) as well as retrograde procedures.

The stent, the flexible mesh respectively, optimally self-adapts to the anatomical conditions of the valve ring and the heart's outflow tract, which thereby achieves a better lateral sealing for the implanted medical instrument.

In the event of the prosthetic valve malfunctioning, the stent with the integrated prosthetic valve can be retracted back through the insertion catheter system and removed completely from the patient's body.

Compared to conventional stent valves, the great degree of flexibility to the wire mesh allows implantation even in the case of highly angular approaches.

The self-expanding wire mesh can be used to replace both the valves of the left as well as the right ventricle and to replace both the atrioventricular valve as well as also the semilunar valve of the heart, since it flexibly adapts to the anatomical conditions and surrounds the old diseased valve.

Reversely pushing in the old diseased valve into the self-expanding wire mesh prevents embolization of portions of the old valve.

The design-contingent integration of retaining elements on the self-expanding wire mesh also allows for same to be explanted again with a special catheter subsequent a successful implantation.

It is pointed out that the realization of the invention is not restricted to the embodiments described with reference to FIGS. 1 to 7, but is also possible in a plurality of other variants.

REFERENCE NUMERALS 1 stent
2 mesh
2' filaments/wire of the mesh
4 mounting
10 distal retention area of the stent
12 beaded portion at the distal retention area
15 center area of the stent
20 proximal retention area of the stent
22 beaded portion at the proximal retention area
30 prosthetic valve
40 catheter system
41 guide wire
50 body's own heart valve
51 pocket of body's own heart valve
52 vascular wall
100 medical instrument

What is claimed is:

1. A replacement valve for use within a human body comprising:
 a valve component; and
 a stent component comprising a first section having a first state during insertion of the stent component and a second, laterally-inverted inside-out state when deployed, a second section for housing the valve component, and a third section,
 wherein the first section, when in the second, laterally inverted inside-out state, is configured to be positioned on a first side of a leaflet of a native valve radially outward of the leaflet and radially inward of a vessel wall when the third section is positioned on a second side of the native valve, opposite the first side, and
 wherein the second section has a cross sectional size smaller than the cross sectional size of the first section and the cross sectional size of the third section.

2. The replacement valve of claim 1, wherein the stent component is further configured such that the second section is capable of engaging an annulus of the native valve.

3. The replacement valve of claim 1, wherein the valve component comprises a biological valve.

4. The replacement valve of claim 1, wherein the valve component comprises a synthetic valve.

5. The replacement valve of claim 1, wherein the stent component is self-expandable.

6. The replacement valve of claim 1, wherein the second section of the stent component follows a contour of the valve component.

7. The replacement valve of claim 1, wherein the stent component comprises a lattice structure comprising a plurality of cells and substantially all of the cells of the stent component are closed cells.

8. The replacement valve of claim 1, wherein the second section is formed from a plurality of independently bendable elements, wherein each bendable element comprises a bending deformation the location of which is determined by the lengths of an attached pair of struts.

9. The replacement valve of claim 1, wherein the first section, the second section, and the third section are positioned at different positions along a central axis of the stent component.

10. The replacement valve of claim 9, wherein the stent component is further configured such that at least a portion of the native valve is pressed against a vascular wall by the second section when the first section is positioned on the first side of the leaflet of the native valve radially outward of the leaflet and radially inward of the vessel wall.

11. The medical device of claim 9, wherein:
 the stent component includes a collapsed state when being inserted into a patient and an expanded state when implanted.

12. A replacement valve for use within a human body comprising:
 a valve component; and
 a stent component comprising a first section, a second section having a first state during insertion of the stent component and a second, laterally-inverted inside-out state when deployed, and a third section,
 wherein the first section comprises an annular groove, and at least a portion of the second section, when in the second, laterally inverted inside-out state, is configured to be positioned on a first side of a leaflet of a native valve radially outward of the leaflet and radially inward of a vessel wall when at least a portion of the third section is positioned on a second side of the native valve opposite the first side.

13. The replacement valve of claim 12, wherein the annular groove is configured to receive and secure circumferentially to an annulus of the native valve.

14. The replacement valve of claim 12, wherein the valve component comprises a biological valve.

15. The replacement valve of claim 12, wherein the valve component comprises a synthetic valve.

16. The replacement valve of claim 12, wherein the stent component is self-expandable.

17. The replacement valve of claim 12, wherein the second section of the stent component follows a contour of the valve component.

18. The replacement valve of claim 12, wherein the stent component comprises a lattice structure comprising a plurality of cells.

19. The replacement valve of claim 12, wherein the stent component includes a collapsed state when being inserted into a patient and an expanded state when implanted.

20. The replacement valve of claim 19, wherein the third section includes a laterally-inverted inside-out state when the stent component is in the expanded state.

21. The replacement valve of claim 19, wherein the stent component is configured to be inserted via a catheter, and the second section is configured to be expanded before the first section.

22. The replacement valve of claim 12, wherein the annular groove extends around the circumference of the stent and has a diameter less that the diameter of the second section and less than the diameter of the third section.

23. A medical device, comprising:
a valve component; and
a stent component, including:
a first portion supporting the valve component,
a second portion connected at a distal end of the first portion having a first state during insertion of the stent component and a second, laterally-inverted inside-out state when deployed, at least a part of the second portion, when in the second, laterally inverted inside-out state, configured to be positioned on a first side of a native valve radially outward of a valve leaflet and radially inward of a vessel wall, and
a third portion connected at a proximal end of the first portion, at least a part of the third portion configured to be positioned on a second side of the native valve, opposite the first side such that the valve leaflet is clamped by the part of the second portion positioned on the first side of the native valve and by the part of the third portion positioned on the second side of the native valve.

24. The medical device of claim 23, wherein the second portion forms the distalmost portion of the stent component, and the third portion forms the proximalmost portion of the stent component.

25. The medical device of claim 23, wherein the stent component is self-expandable.

26. The medical device of claim 23, wherein the valve component is includes a biological valve.

27. The medical device of claim 23, wherein the valve component includes a synthetic valve.

28. The medical device of claim 23, wherein the stent component includes a lattice structure comprising a plurality of expandable cells.

29. The medical device of claim 23, wherein:
the stent component includes a collapsed state when being inserted into a patient and an expanded state when implanted.

30. The medical device of claim 23, wherein the stent component is configured to be inserted into a patient via a catheter.

31. The medical device of claim 23, wherein the stent component is configured to be explanted from a patient via a catheter.

32. The medical device of claim 31, wherein the stent further includes an explantation element configured to be selectively engaged by the catheter to explant the stent component.

33. The medical device of claim 32, wherein the explantation element is a ring connected to the third portion.

34. A medical device, comprising:
a valve component; and
a stent component including a distal section having a first state during insertion of the stent component and a second, laterally-inverted inside-out state when deployed, proximal section, and a middle section disposed between the distal and proximal sections and supporting the valve component;
wherein a portion of the distal section, when in the second, laterally inverted inside-out state, is configured to be positioned on a first side of a native valve radially outward of a valve leaflet and radially inward of a vessel wall, a portion of the middle section is configured to be positioned within the annulus of the native valve, and a portion of the proximal section is configured to be positioned on a second side of the native valve, opposite the first side; and
wherein the valve leaflet is clamped by the portion of the distal section positioned on the first side of the native valve and by the portion of the proximal section positioned on the second side of the native valve.

35. The medical device of claim 34, wherein the stent component is configured to compress the native valve against a vascular wall.

36. The medical device of claim 34, wherein the middle section includes an annular groove.

37. The medical device of claim 34, wherein the stent component is self-expandable.

38. The medical device of claim 34, wherein the valve component includes a biological valve.

39. The medical device of claim 34, wherein the valve component includes a synthetic valve.

40. The medical device of claim 34, wherein the valve stent includes a lattice structure including a plurality of expandable cells.

41. The medical device of claim 34, wherein the middle section has a cross sectional size that is smaller than the cross sectional size of the distal and proximal sections.

42. The medical device of claim 34, wherein the stent component includes a collapsed state when being inserted into a patient and an expanded state when implanted.

* * * * *

UNITED STATES PATENT AND TRADEMARK OFFICE
CERTIFICATE OF CORRECTION

| | | |
|---|---|---|
| PATENT NO. | : 8,062,355 B2 | Page 1 of 1 |
| APPLICATION NO. | : 11/592369 | |
| DATED | : November 22, 2011 | |
| INVENTOR(S) | : Hans-Reiner Figulla et al. | |

It is certified that error appears in the above-identified patent and that said Letters Patent is hereby corrected as shown below:

In the Claims:

Claim 22, col. 11, line 35, "less that the diameter" should read --less than the diameter--.

Claim 26, col. 11, line 63, "component is includes" should read --component includes--.

Signed and Sealed this

Thirty-first Day of January, 2012

David J. Kappos
*Director of the United States Patent and Trademark Office*